United States Patent [19]

Schaberg et al.

[11] Patent Number: 4,545,389
[45] Date of Patent: Oct. 8, 1985

[54] DISPOSABLE PHYSIOLOGICAL PRESSURE SENSING SYSTEM

[75] Inventors: Richard R. Schaberg; James E. Cole, both of Ventura, Calif.

[73] Assignee: Gould Inc., Rolling Meadows, Ill.

[21] Appl. No.: 398,399

[22] Filed: Jul. 14, 1982

[51] Int. Cl.⁴ .............................................. A61B 5/00
[52] U.S. Cl. ................................... 128/748; 128/675; 73/715
[58] Field of Search ................................. 128/672–675, 128/748; 604/52–53; 73/706, 715

[56] References Cited

U.S. PATENT DOCUMENTS

| | | | |
|---|---|---|---|
| 2,535,998 | 12/1950 | Bierman | 128/675 |
| 2,600,324 | 6/1952 | Rappaport | 73/749 |
| 2,866,453 | 12/1958 | Jewett | 128/674 |
| 2,976,865 | 3/1961 | Shipley | 128/675 |
| 3,122,136 | 2/1964 | Murphy | 128/673 |
| 3,350,944 | 11/1967 | De Michele | 128/675 |
| 3,444,736 | 5/1969 | Stedman | 338/4 |
| 3,610,228 | 10/1971 | Temkin | 128/748 |
| 3,648,687 | 3/1972 | Ramsey, III | 128/673 |
| 3,675,891 | 7/1972 | Reynolds et al. | 128/673 X |
| 3,720,201 | 3/1973 | Ramsey | 128/748 |
| 3,724,274 | 4/1973 | Millar | 128/675 X |
| 3,818,765 | 6/1974 | Eriksen | 73/395 |
| 3,865,100 | 2/1975 | Kanai et al. | 128/675 |
| 3,894,435 | 7/1975 | Shimada et al. | 338/4 |
| 3,970,982 | 7/1976 | Kurtz et al. | 338/4 |
| 3,999,542 | 12/1976 | Shaw | 604/52 |
| 4,051,451 | 9/1977 | Kurtz et al. | 338/4 |
| 4,072,056 | 2/1978 | Lee | 128/675 X |
| 4,141,253 | 2/1979 | Whitehead | 73/727 |
| 4,192,303 | 3/1980 | Young et al. | 604/250 |
| 4,226,124 | 10/1980 | Kersten | 128/748 X |
| 4,245,636 | 1/1981 | Sparks et al. | 604/249 |
| 4,274,423 | 6/1981 | Mizuno et al. | 128/675 |
| 4,291,702 | 9/1981 | Cole et al. | 128/675 |
| 4,300,571 | 11/1981 | Waldbillig | 128/673 |
| 4,341,224 | 7/1982 | Stevens | 128/675 |
| 4,365,635 | 12/1982 | Bowman | 604/53 X |
| 4,398,542 | 8/1983 | Cunningham et al. | 128/748 X |
| 4,431,009 | 2/1984 | Marino, Jr. et al. | 128/675 X |
| 4,462,409 | 7/1984 | Pace et al. | 128/748 X |

OTHER PUBLICATIONS

Moss; "Simple Inexpensive Unit for Direct Arterial Press. Monitoring".

*Primary Examiner*—Lee S. Cohen
*Assistant Examiner*—Angela D. Sykes

[57] ABSTRACT

A physiological pressure sensing and monitoring system including a sterile throwaway pressure transducing device. The device includes a pressure transducer mounted together with a flow control valve in a housing. The device includes a first connector for connecting the device to a source of sterile solution, a second connector for electrically connecting the pressure transducer to a monitoring device, and a third connector for selectively connecting the device to a catheter inserted into a patient's circulatory system. The device, including the connectors, is made to be low cost so as to permit the entire device to be installed and discarded as a unit so as to constitute a throwaway pressure sensing and flow regulating means. A number of different embodiments of the pressure transducer are disclosed, each of which constitutes a low cost, accurate pressure transducing means arranged to have high electrical isolation relative to the fluid in a pressure chamber of the housing, the pressure of which is continuously sensed by the transducer. In one embodiment, the force collector for transmitting the pressure force to the strain gage is formed as a one-piece unit. In a number of the embodiments, the elements are formed separately and bonded together.

16 Claims, 29 Drawing Figures

DISPOSABLE PHYSIOLOGICAL PRESSURE SENSING SYSTEM

BACKGROUND OF THE INVENTION

1. Field of the Invention

This invention relates to physiological pressure sensing systems, and in particular to such a system utilizing a disposable pressure transducer.

2. Description of the Background Art

An improved flow control apparatus for use in liquid flow systems, such as for monitoring of blood pressure in humans and other animals, is disclosed in U.S. Pat. No. 4,291,702, of James E. Cole et al, which patent is owned by the assignee hereof. As disclosed therein, the flow control apparatus is adapted for use with fluid flow catheters, such as used in invasive connection as by insertion into a patient's blood vessel. In normal use in such systems, the catheter is provided with a sterile isotonic solution which is caused to flow through the catheter into the patient at a low flow rate sufficient to maintain the catheter open and unclogged as by blood cells and the like at the inserted end of the catheter.

As further pointed out in the Cole et al patent, the catheter system is firstly flushed of air before insertion of the catheter into the patient. To permit the system to be rapidly filled with the sterile solution which is used to flush the system of air, the catheter flushing apparatus of said patent further is arranged to selectively permit a high flow rate of the solution from the source to the catheter.

In one embodiment of the structure disclosed in the Cole et al patent, a flexible diaphragm is extended across an opening to the pressure chamber of the housing of the apparatus. Means are provided for connecting a fluid actuated transducer to the housing so that deflections of the diaphragm cause corresponding fluid pressure transmissions to the transducer.

A problem has arisen in the use of such systems relative to the high expense and unreliability of the pressure transducers before employed in such systems. Such transducers have been quite expensive in order to provide the necessary accuracy. As the transducers must be cleaned and sterilized from time to time, the useful life thereof has been relatively short. Such transducers further have been found to become inoperative as a result of the cleaning and sterilization processes. Such inoperativeness presents a particularly vexatious problem in that it normally occurs at the critical time of setting up the system with the patient as testing of the apparatus is normally conducted prior to the cleaning and sterilization steps because of the impracticality of testing subsequent thereto.

Further, the use of the reusable pressure transducers may cause cross-contamination and spreading of infection where complete cleaning and sterilization are not achieved.

SUMMARY OF THE INVENTION

The present invention comprehends an improved physiological pressure monitoring system which eliminates the high cost and unreliability problems of the prior art systems by the provision of an improved throwaway component including the fast-slow flow control means and the pressure transducer means in a single housing.

The invention comprehends the provision of the system as a low cost, high accuracy transducer effectively permitting throwaway use of the device so that the device may be used with a single patient only, thereby completely avoiding cross-contamination and infection.

The invention comprehends that the device further include means for connecting the source of sterile isotonic solution thereto and means for connecting the patient catheter thereto.

Still further, the illustrated device includes electrical connection means for connecting electrical output means of the pressure transducer to an external monitor and the like.

The invention comprehends the inclusion of the connecting means as portions of the throwaway device.

The means for controlling solution flow from the source, such as an elevated bag or container, further includes flow restrictor means which maintains the pressure chamber of the device substantially at the patient's blood pressure, notwithstanding the continual delivery of solution at a low rate therethrough to the catheter for maintaining the catheter unclogged, as discussed above.

The invention comprehends the provision of such a device wherein the pressure transducer sensing means is electrically isolated from the fluid in the pressure chamber so as to effectively prevent damage to the pressure transducer as by application of high voltages and transient electrical pulses of 400 to 500 joules such as may be applied to the patient in effecting certain treatments thereof. Alternatively, the electrical isolation of the transducer from the pressure chamber avoids transfer of electrical current from the external monitoring system and, thus, effectively prevents fibrillation of the patient's heart, such as by a short occurring in the external system.

The invention further comprehends the provision in the throwaway device of pressure relief means for preventing high pressure conditions which may appear in the pressure chamber from damaging the pressure transducer.

The arrangement of the device as a throwaway device permits it to be packaged in sterile condition for sterile storage until desired use. At that time, the sterile sealed package is opened and the system filled with sterile isotonic solution to eliminate any air pockets therein and permit facilitated invasive connection to the patient.

The device provides a complete interconnection system between the source of sterile solution, the electrical monitoring apparatus, and the patient, and thus, completely eliminates the possibility of cross-contamination, as well as assuring that a reliable new system is available for immediate use.

The invention comprehends the forming of the housing and other components of the system from low cost molded synthetic resins, such as polycarbonate.

It is desirable that the synthetic resins have high strength, chemical and electrical resistance, and dimensional stability.

In the illustrated embodiment, the pressure transducer utilizes a strain gage comprising a diffused pattern on a single crystal silicon beam, it being understood that other forms of pressure transducers providing suitable electrical signal outputs may be employed within the scope of the invention.

The invention comprehends that the major spring restraint in the pressure transducer be provided by the beam. A compliant diaphragm is provided in the illustrated embodiment, with suitable link connecting means between the diaphragm and beam forming a portion of the force collector structure.

Calibration of the pressure transducer is effected in the illustrated embodiment by suitable trimming of resistors provided in the electrical connection means for facilitated, low cost calibration.

The electrical connector calibration means provides sensitivity normalization and thermal error compensation.

The transducer includes a strain relief and a flexible cable of electrical conductors connected to the strain gage by suitable fine wires.

The invention comprehends the provision of such a transducer wherein the member of major restraint is arranged to be self-protecting from overpressure, permitting omission of an overpressure safety stop.

In the illustrated embodiment the connection to the catheter from the pressure chamber within the housing includes a multiple connection stopcock for selectively connecting the system in a plurality of different paths.

In the illustrated embodiment, the stopcock is formed integrally with the housing as part of the low cost throwaway device.

The invention comprehends the use of different forms of pressure transducers mounted in the housing.

In the illustrated embodiments, the pressure transducers include a force collector including a diaphragm, a frame, and a link for connecting the diaphragm to the deflectible beam.

In the illustrated embodiments, the beam is provided with strain gage means. In one form, the beam is formed of silicon, with a resistive strain gage grid fused thereinto.

The beam, in the illustrated embodiments, is mounted to the frame by a strain isolator for preventing strain which may be induced in the frame from affecting the strain gage means.

In the illustrated embodiment, the external control resistor comprises a thin film resistor which is selectively trimmed by a laser trimming operation to provide the desired calibration of the pressure transducer.

The structure of the device is extremely simple so that the elements may be formed by automatic manufacturing processes to further reduce the cost of the device, permitting the one-time throwaway use thereof.

Further low cost manufacture is effected in one embodiment of the invention by forming the three elements of the force collector as a one-piece unit.

Further low cost manufacture is effected, in the illustrated embodiment, by forming the beam as a wafer element having a thickness of approximately 0.01 inches.

The throwaway pressure monitoring device of the present invention is extremely simple and economical of construction while yet providing the highly desirable features discussed above.

BRIEF DESCRIPTION OF THE DRAWING

Other features and advantages of the invention will be apparent from the following description taken in connection with the accompanying drawing wherein.

DESCRIPTION OF THE PREFERRED EMBODIMENTS

Figures 3, 4, 5:
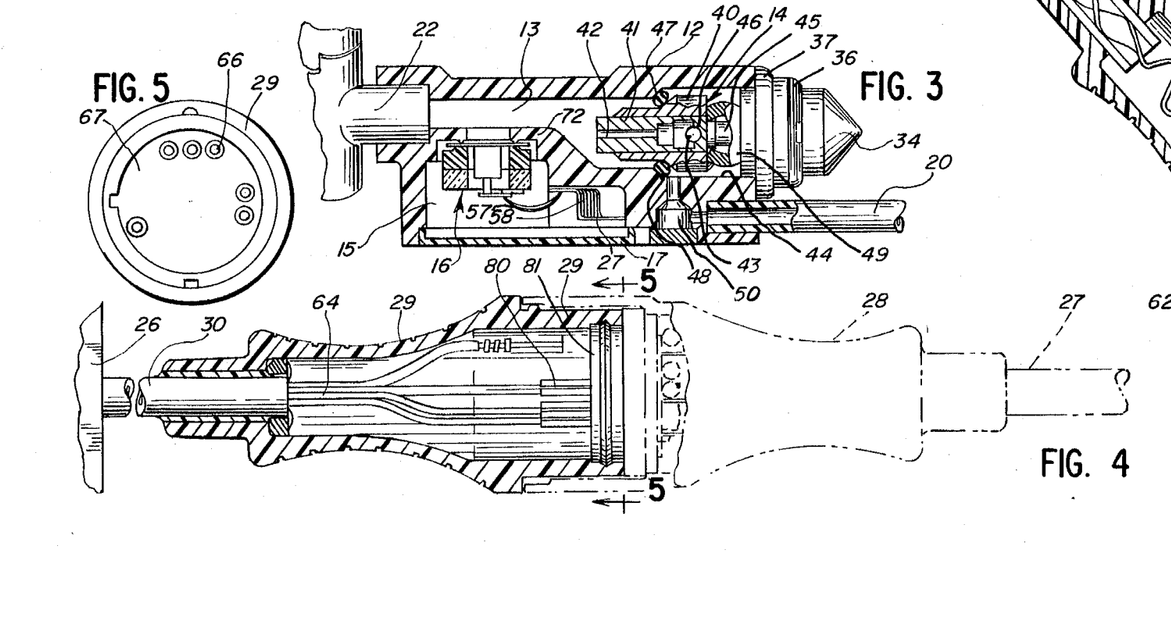
FIG. 3 is a fragmentary vertical section taken substantially along the line 3—3 of FIG. 2.
FIG. 4 is a fragmentary diametric section illustrating the connection of a reusable connector associated with the monitoring apparatus, with the disposable electrical connector portion of the throwaway device.
FIG. 5 is a transverse section taken substantially along the line 5—5 of FIG. 4.

In the exemplary embodiment of the invention as shown in the drawing, a disposable, physiological pressure sensing system generally designated 10 is shown to comprise a device 11 having a housing 12 which, as seen in FIG. 3, defines a pressure chamber 13, at one end of which is received a flow control valve 14.

As further illustrated in FIG. 3, housing 12 further defines a transducer chamber 15 in which is mounted a pressure transducer 16. Chamber 15 is selectively closed by a closure element 17.

Figure 1:
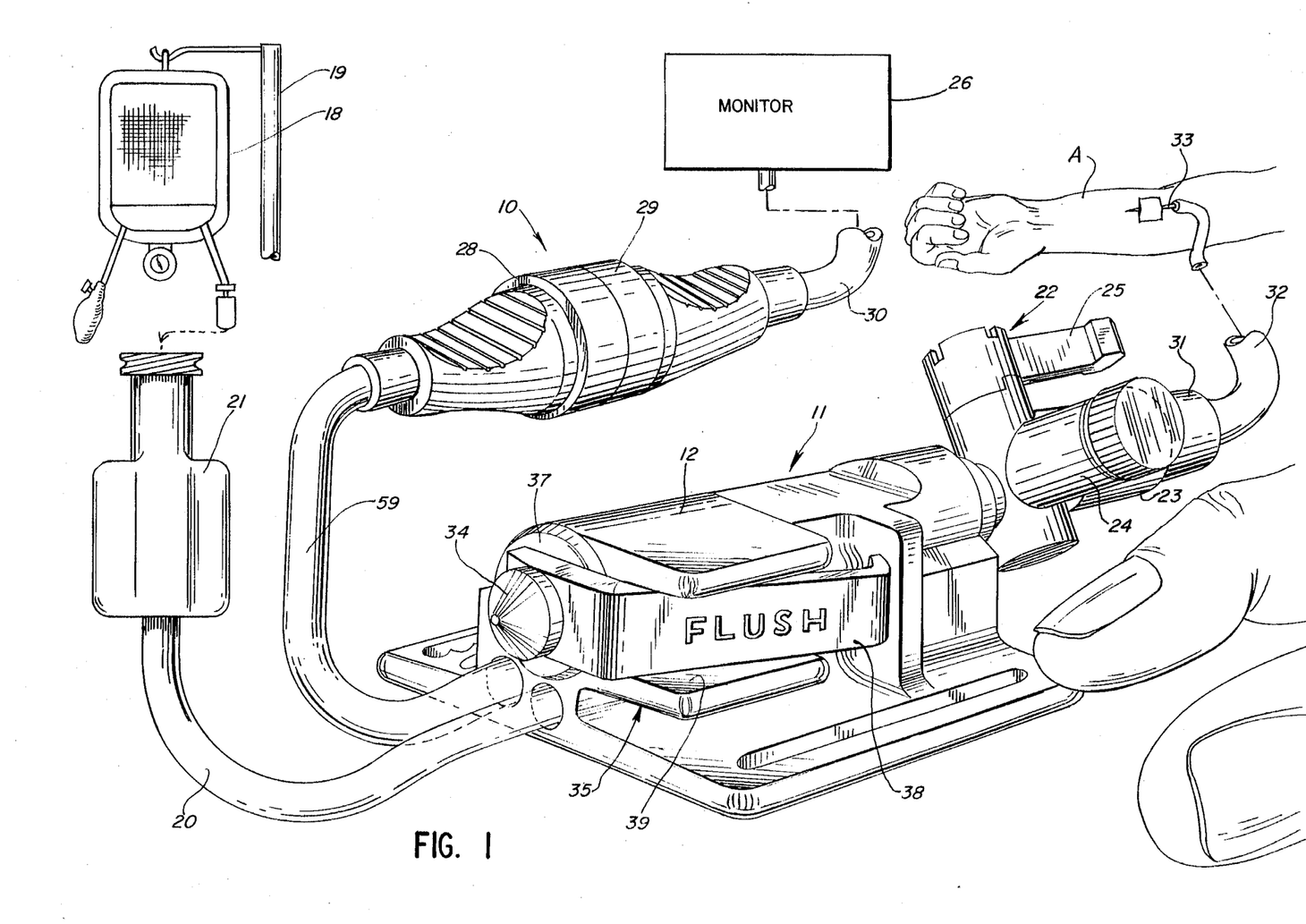
FIG. 1 is a broken perspective view of a disposable physiological pressure sensing system embodying the invention for association with a source of sterile fluid, monitoring apparatus, and a catheter adapted to be inserted into a patient's circulatory system.

Sterile isotonic solution, such as saline solution, is provided to chamber 13 from an external pressurized source, such as bag device 18 illustrated in FIG. 1, carried on a suitable standard 19 suitably adjusted to provide a controlled pressure delivery (conventionally at approximately 300 millimeters of mercury) of the solution therefrom through a conduit 20 connected to the bag device 18 by a conventional connector 21. The sterile solution is delivered from the pressure chamber 13 through a connector generally designated 22, which, in the illustrated embodiment, comprises a stopcock, selectively connecting the pressure chamber to a Luer connector 23, or a bypass connector 24, as a result of suitable manipulation of a handle 25.

Pressure transducer 16 provides an electrical output signal corresponding to the pressure of fluid in pressure chamber 13, which is transmitted to an external monitor 26 of conventional construction through a cable 27 terminating in a connector 28. Connector 28 is adapted to have readily separable connection to a connector 29 connected to monitor 26 through a cable 30. Flow of saline solution from connector 23 is effected through a connector 31 at the distal end of a conduit 32 terminating in a catheter 33 providing an invasive connection to the patient when inserted into a blood vessel of a patient.

Thus, the boundaries of the device 11 are defined by the connectors 21, 28 and 23 so that the device may be provided as an integral assembly readily connected into the system wherein the external components comprise the saline source bag device 18, the monitoring apparatus 26, and the connection 31 to the conduit connected to the patient.

Figure 2:
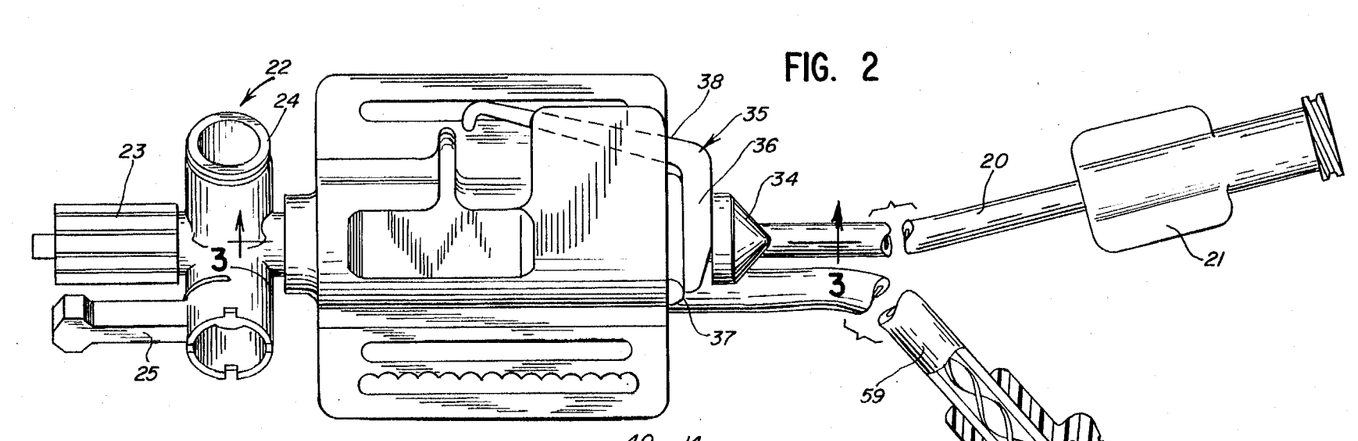
FIG. 2 is a fragmentary plan view of the throwaway device.

As further illustrated in FIG. 1, flow control valve 14 is provided with an outer connector 34 engaged by an angle operator 35 which, when depressed, pulls the valve to an open position, permitting a high rate of flow of the saline solution from source 18 into pressure chamber 13. As best seen in FIG. 2, operator 35 includes an apertured end portion 36 extending between the connector 34 and a cap 37 on housing 12 sealing the end of the pressure chamber inlet portion 44. A finger engageable portion 38 extends angularly to portion 36 and is received in a space 39 so that when the portion 38 is urged inwardly toward housing 12, portion 36 is rocked outwardly to urge connector 34 outwardly and thereby pull the valve 14 to an open position.

More specifically, valve 14 is generally similar to and functions generally similar to the fast flush valve of the above discussed U.S. Pat. No. 4,291,702, which patent is incorporated by reference herein. Briefly, however, valve 14 is defined by a valve body 40 having a through bore receiving a cylindrical insert 41 provided with a capillary bore 42 illustratively having a diameter of approximately 0.002 inches. At its outer end, the insert is provided with radially opening passages 43 for conducting saline solution from inlet portion 44 of pressure chamber 13 into insert 41 for metered flow outwardly through capillary bore 42 into pressure chamber 13.

As further illustrated in FIG. 3, connector 34 is provided with a stem 45 bonded to the outer end 46 of insert 41, so that when connector 34 is urged outwardly by operator 35, as discussed above, insert 41 and body 40 are pulled outwardly to disengage the body from an annular O-ring seal 47 and thereby provide a flow path from inlet portion 44 around the seal to pressure chamber 13 and stopcock 22. The valve is biased to the closed position wherein body 40 seats against O-ring 47 which, in turn, is urged against a frustoconical shoulder 48 between inlet portion 44 and pressure chamber 13 by a resilient tube 49 extending axially between valve body 40 and cap 37. As shown in FIG. 3, the length of tube 49 is slightly greater than the space between body 40 and cap 37 so that the tube is under compression, thereby providing the desired biasing of the valve to the closed disposition illustrated in FIG. 3 and sealing of the cap to the valve body 40 about the stem 45.

As further shown in FIG. 3, supply conduit 20 is connected to pressure chamber inlet portion 44 through a passage 50 opening to portion 44 adjacent O-ring 47.

The resiliency of tube 49 is preselected to permit outward movement of the valve body as a result of an increase in pressure in pressure chamber 13 to an undesirably high pressure so as to relieve the pressure by directing the isotonic saline solution to the bag 18 and thereby to prevent damage to the transducer from such high pressure conditions or surges.

As indicated briefly above, the invention comprehends the provision in housing 12 in combination with the flow control valve 14 of the pressure transducer 16, permitting the pressure transducer to be included with the other components of the device for throwaway use of the entire system by virtue of the low cost construction thereof. In the illustrated embodiment, as shown in FIGS. 6–9, the pressure transducer includes a deflectible beam 51 having one end 52 secured to a strain isolator 53 as by electrostatic bonding 54, or suitable adhesive means. Beam end 52 is provided with a wheatstone bridge strain gage 55. In the illustrated embodiment, the strain gage resistance grid is fused into the beam which, illustratively, may be formed of a suitable deflectible material, such as silicon, etc. The beam preferably has a wafer thickness of approximately 0.01 inches for facilitated manufacture and defines the major restraint component of the pressure transducer.

Figures 6, 7:
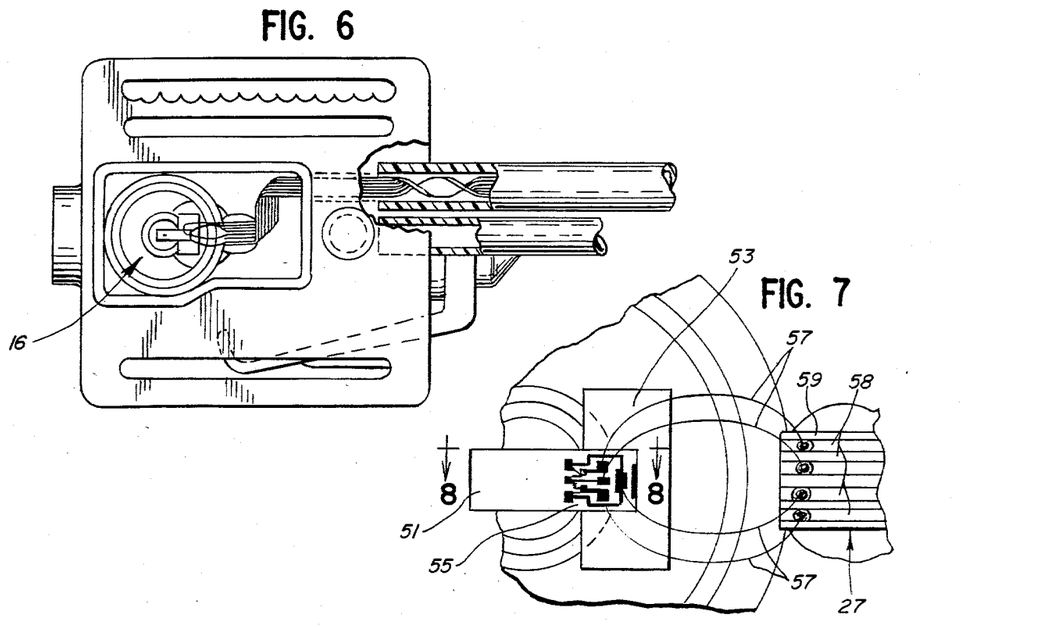
FIG. 6 is a bottom plan view of the device with a portion broken away to facilitate illustration of the connections to the housing.
FIG. 7 is a fragmentary enlarged bottom plan view of the strain gage and connections to the electrical conductor cable.
Figure 8:
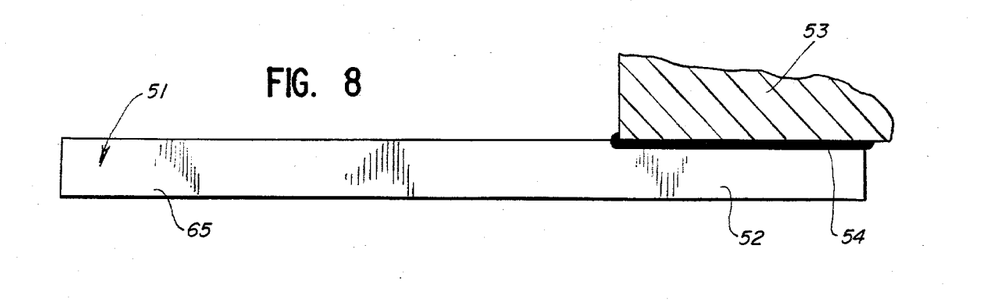
FIG. 8 is a fragmentary enlarged vertical section taken substantially along the line 8—8 of FIG. 7 illustrating the mounting of the beam to the isolator.
Figure 9:
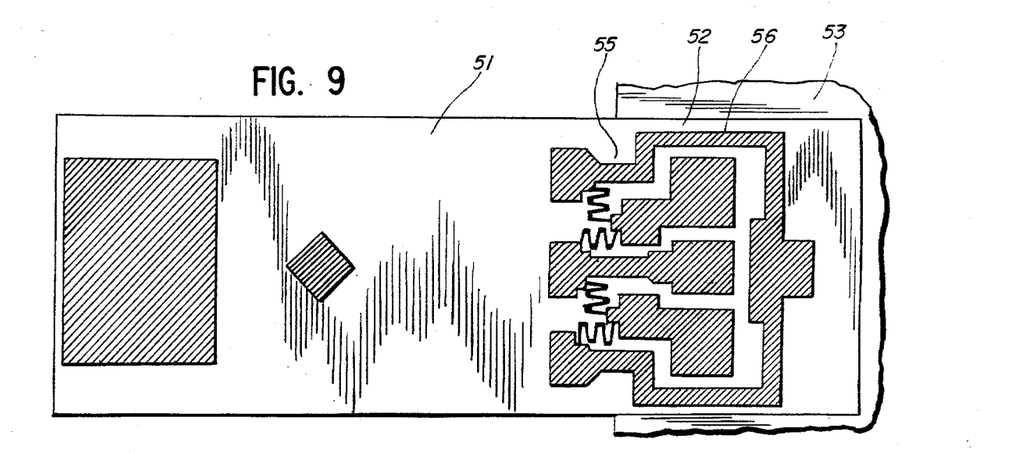
FIG. 9 is a fragmentary enlarged bottom plan view of the strain gage bridge circuit on the beam.

As further indicated in FIG. 9, the strain gage bridge includes a plurality of pads 56 to which fine gold alloy wires 57 are electrically connected at one end. As shown in FIG. 7, the opposite end of wires 57 are electrically connected to flat conductors 58 of cable 27 received in a flexible conduit 59.

As illustrated in FIG. 2, the distal end of cable 27 is received in a connector head 60 and connected to a connector plate 61 thereof through calibrating resistors 62. The calibrating resistors are calibrated by laser trimming in a conventional manner so as to calibrate the pressure transducer accurately for clinical use. As further shown in FIG. 2, the head 60 defines a distal socket portion 63 for receiving the male connector 29 (see FIG. 4). The male connector houses the end of a cable 64 for providing connection from connector plate 61 to the monitor apparatus 26, as illustrated in FIG. 4. As indicated above, the male connector 29 and cable 30 are reusable components of the overall system, being separable from connector 28 for disposal of the device 11 as a whole.

In the illustrated embodiment, connector plate 61 is provided with a plurality of connector pins 79 aligned with and adapted to be received in suitable female connectors 80 in a connector plate 81 in connector head 29.

Figure 29:
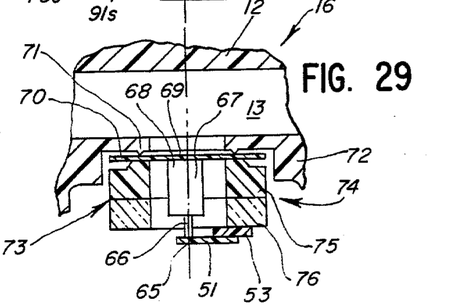

The preferred embodiment of pressure transducer 16 is illustrated in FIG. 29. As shown therein, the distal end 65 of beam 51 is connected to a projecting pin portion 66 of a small diameter link 67 having its opposite end 68 connected to the midportion 69 of a diaphragm 70. Diaphragm 70 is bonded to an annular rib 71 on housing wall 72 separating pressure chamber 13 from transducer chamber 15.

A frame generally designated 73 extends coaxially oppositely of rib 71 from the opposite face of the diaphragm, and in the pressure transducer 74 illustrated in FIG. 29 is defined by a pair of coaxial annular portions 75 and 76. As shown, isolator 53 is mounted to the outer frame portion 76.

Diaphragm 70 is formed of a compliant material so as to be highly flexible, and in the illustrated embodiment, comprises a disc of polycarbonate having a thickness of 0.002 inches. Frame portion 75, in the illustrated embodiment, comprises an annular element formed of molded polycarbonate and link 67 comprises a cylindrical element formed of molded polycarbonate. The link, diaphragm and frame portion may be molded as a one-piece force collector structure. Alternatively, the link, diaphragm and frame portion may be separately formed and secured together. Thus, the frame portion 75 may be secured to the diaphragm by a cyanoacrylate bonding agent, and the diaphragm may be sealed to the link by suitable polycarbonate solvent. The diaphragm, in turn, may be secured to the housing rib 71 by a suitable polycarbonate solvent.

Isolator 53 may be secured to the beam end 52 by an epoxy adhesive. In the illustrated embodiment, frame portion 76 is formed of glass and beam end 52 is bonded thereto with an epoxy adhesive. Frame portion 76 is bonded to frame portion 75, in turn, with an epoxy adhesive. As indicated above, the beam comprises a 0.01 inches thick wafer of a suitable relatively stiff material so as to provide a major restraint portion of the force transducer.

Figure 10:
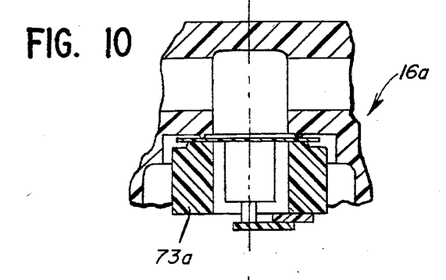
FIGS. 10–29 are diametric sections illustrating different forms of pressure transducer structures embodying the invention.

Additional embodiments of pressure transducers within the scope of the invention are illustrated in FIGS. 10–28. Thus, as seen in FIG. 10, a pressure transducer generally designated 16a is shown to comprise a pressure transducer generally similar to transducer 16, but having a one-piece frame 73a formed entirely of molded polycarbonate resin.

Figure 11:
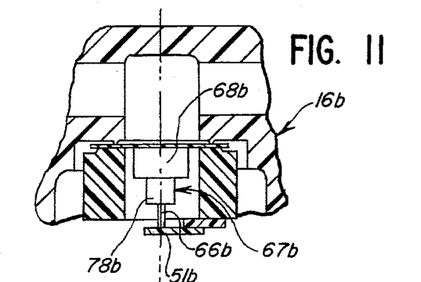

In FIG. 11, another form of pressure transducer embodying the invention is shown to comprise a pressure transducer 16b which is generally similar to pressure transducer 16a but wherein the link 67b includes a large diameter portion 68b connected to the diaphragm and a small diameter portion 78b connected to the pin 66b in turn connected to the beam 51b. The link 67b, however, is formed as a one-piece stepped element of polycarbonate resin.

Figure 12:
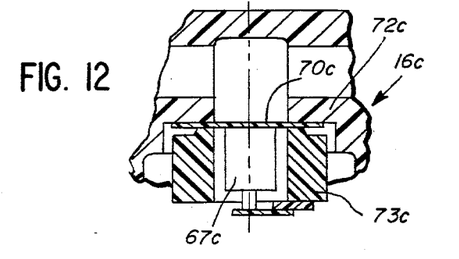

Referring now to FIG. 12, still another pressure transducer generally designated 16c embodying the invention is shown to comprise a structure generally similar to that of pressure transducer 16a except that the diaphragm 70c is bonded to the frame 73c, the housing wall 72c, and the link 67c by a cyanoacrylate bonding agent.

Figure 13:
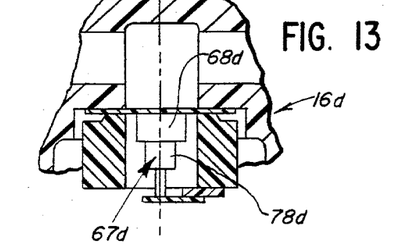

A further modified form of pressure transducer 16d is illustrated in FIG. 13 to comprise a pressure transducer similar to pressure transducer 16c except that the link 67d comprises a stepped link having a large diameter portion 68d and a reduced diameter portion 78d.

Figure 14:
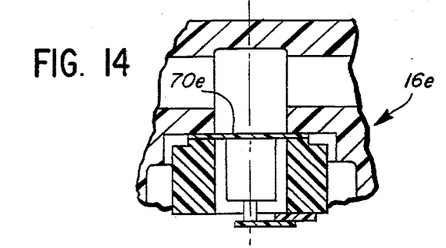

Referring to the embodiment of FIG. 14, a pressure transducer generally designated 16e is shown to comprise a pressure transducer similar to pressure transducer 16c except that the diaphragm 70e is formed of polyurethane.

Figure 15:
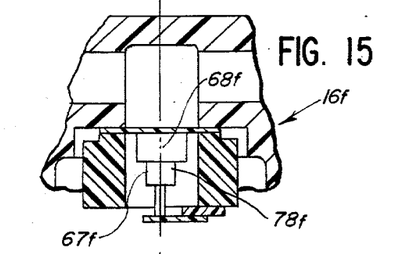

The pressure transducer generally designated 16f of FIG. 15 is similar to pressure transducer 16e except that the link 67f is provided with a large diameter portion 68f and a small diameter portion 78f similar to the link 67b of FIG. 11.

Figure 16:
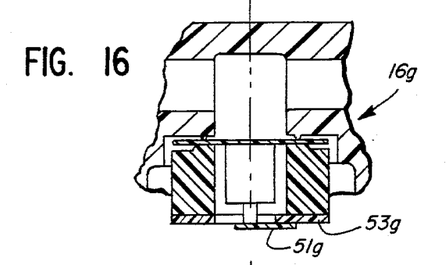

Referring now to FIG. 16, a further modified form of pressure transducer designated 16g is shown to comprise a pressure transducer generally similar to transducer 16c but wherein the isolator comprises a washer-like ring 53g. In the illustrated embodiment, the ring is formed of Invar metal and has a thickness of approximately 0.02 inches. The beam 51g is bonded to the Invar ring by suitable material, such as epoxy adhesive.

Figure 17:
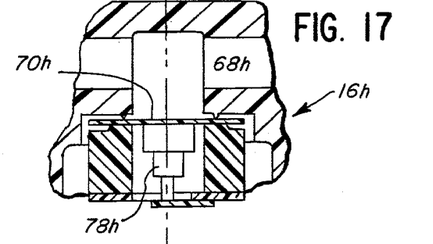

A pressure transducer generally designated 16h is illustrated in FIG. 17 and comprises a pressure transducer generally similar to pressure transducer 16g but wherein the link includes a small diameter portion 78h and a large diameter portion 68h solvent bonded to the diaphragm 70h.

Figure 18:
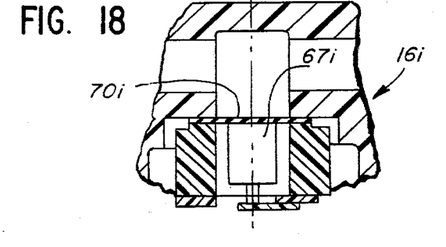

Referring now to FIG. 18, still another form of pressure transducer generally designated 16i embodying the invention is shown to comprise a pressure transducer similar to pressure transducer 16g but wherein the diaphragm 70i is formed of silicone rubber and has a thickness of approximately 0.005 inches. The diaphragm is bonded to the link 67i by suitable epoxy resin.

Figure 19:
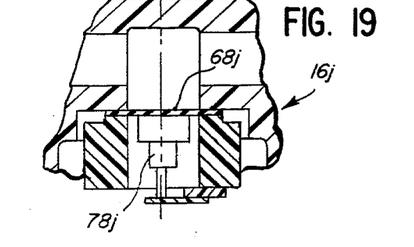

In FIG. 19, still another form of pressure transducer generally designated 16j is shown to comprise a pressure transducer generally similar to pressure transducer 16i but wherein the link includes a small diameter portion 78j and a large diameter portion 68j bonded to the diaphragm by a suitable epoxy resin.

Figures 20, 21, 22, 23:
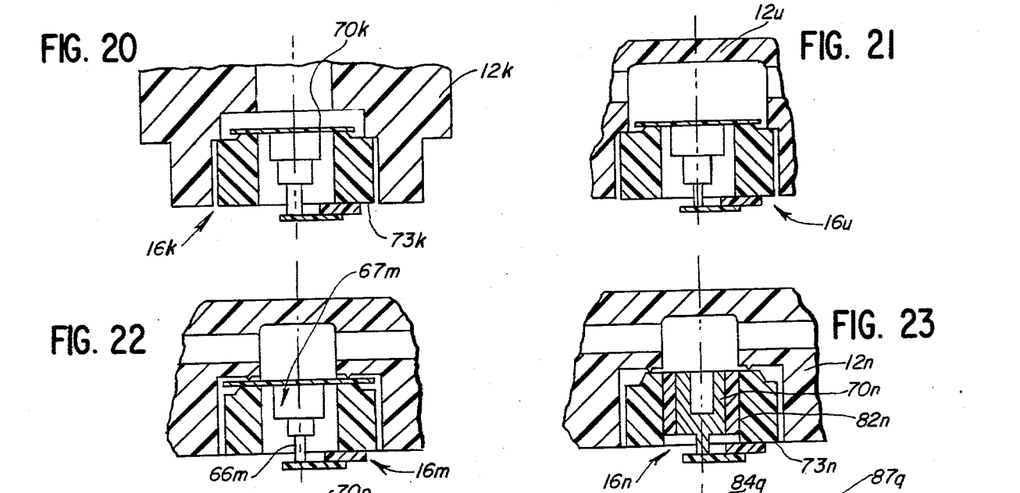

Referring now to the embodiment of FIG. 20, a pressure transducer generally designated 16k is shown to comprise a pressure transducer generally similar to transducer 16b but wherein the housing 12k defines a cap wherein the diaphragm 70k is spaced therefrom, and the frame 73k is solvent-bonded to the cap.

A pressure transducer generally designated 16u is illustrated in FIG. 21 to comprise a pressure transducer similar to transducer 16k but wherein the housing 12u defines an edge mounting of the pressure transducer.

In FIG. 22, a pressure transducer generally designated 16m is shown to comprise a pressure transducer generally similar to pressure transducer 16b but wherein the pin portion 66m of the link 67m has a reduced diameter so as to have increased flexibility.

Still another form of pressure transducer generally designated 16n is illustrated in FIG. 23 to comprise a pressure transducer wherein the diaphragm is omitted and replaced by a piston 70n reciprocably movable in a tubular gel seal 82n self-bonded to the frame 73n. The frame is solvent bonded to the housing 12n.

As illustrated in FIG. 23, the piston may be configured to be relatively rigid. As will be obvious to those skilled in the art, alternatively the piston may have a thinner configuration to provide greater flexibility therein.

Figure 24:
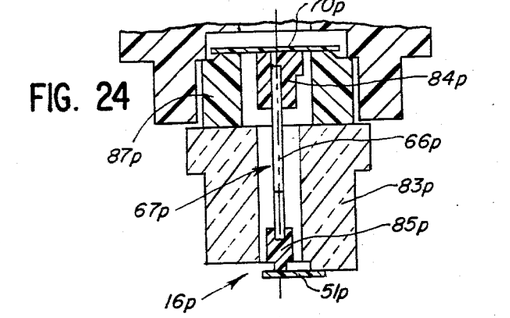

Referring to the embodiment of FIG. 24, a pressure transducer generally designated 16p is shown to comprise a pressure transducer which is similar to transducer 16k but wherein the frame includes an outer portion 83p formed of glass, permitting the elimination of the isolator by the epoxy bonding of the beam 51p to the outer end of the glass frame portion 83p. Further, as shown in FIG. 24, the link generally designated 67p includes a small diameter, intermediate pin portion 66p connected to the diaphragm 70p by a retainer 84p and to the beam by a retainer 85p. The pin portion 66p is preferably formed of glass and the retainers, in the illustrated embodiment, are formed of polycarbonate resin.

Figure 25:
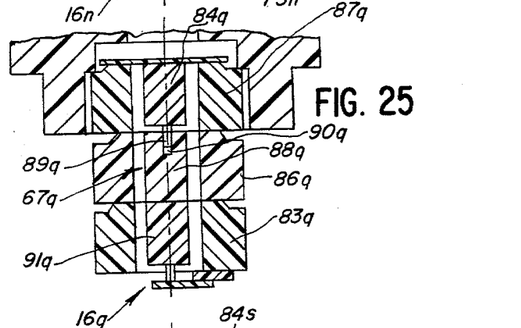

A further modified form of pressure transducer generally designated 16q is illustrated in FIG. 25. As shown therein, the pressure transducer is similar to pressure transducer 16p but includes an intermediate frame portion 86q and an outer frame portion 83q disposed in series with the inner frame portion 87q. In the embodiment of FIG. 25, the frame portions are formed of polycarbonate and are bonded together by a suitable epoxy resin. The link pin generally designated 67q includes an inner portion 84q, an intermediate portion 91q, and an outer portion 83q, each of which is formed of molded polycarbonate resin, the link portions being bonded together by a suitable epoxy resin adhesive. As shown in FIG. 25, the inner link portion 84q may be provided with a reduced diameter connecting portion 89q received in a recess 90q of the intermediate link portion 88q.

Figure 26:
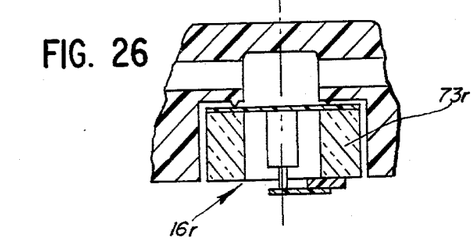

Referring now to the embodiment of FIG. 26, a pressure transducer generally designated 16r is shown to comprise a pressure transducer generally similar to transducer 16a but wherein the frame 73r is formed of ground glass in a suitable binder.

Figure 27:
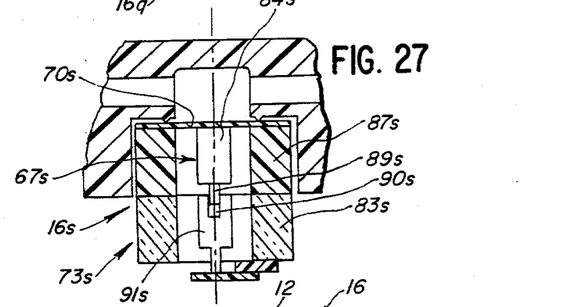

Still another form of pressure transducer generally designated 16s is illustrated in FIG. 27 to comprise a pressure transducer generally similar to pressure transducer 16r but wherein the frame generally designated 73s includes an inner portion 87s and an outer portion 83s. In the illustrated embodiment, frame portion 87s is formed of polycarbonate resin and frame portion 83s is formed of ground glass in a suitable binder, the frame portions being bonded together by a suitable epoxy resin adhesive. As further shown in FIG. 27, the link generally designated 67s includes an inner portion 84s bonded to the diaphragm 70s and an outer portion 91s interconnected by a small diameter portion 89s on link portion 84s received in a recess 90s in link portion 91s.

Figure 28:
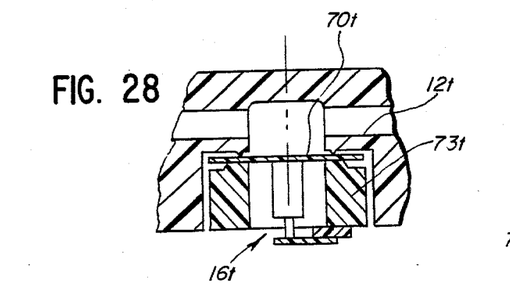

Still another form of pressure transducer generally designated 16t is illustrated in FIG. 28 to comprise a pressure transducer generally similar to pressure transducer 16a but wherein the diaphragm 70t is solvent-bonded to the frame 73t, as well as to the housing 12t. Alternatively, the diaphragm 70t may be bonded to the frame 73t by a cyanoacrylate adhesive within the scope of the invention.

Each of the additional embodiments of the invention as disclosed in FIGS. 10-28 as discussed above, is similar to the preferred embodiment pressure transducer 16 shown in FIG. 29 except for the differences discussed above. Broadly, the different embodiments utilized different configurations of the frame and link and different methods of effecting the bonding together of the elements of the pressure transducer. However, each of the embodiments is similar in providing a pressure-responsive movable element acting on the distal end of a cantilevered beam which is mounted in substantially spaced relationship to the movable element so as to have high electrical resistance therebetween. The movable element is connected to the beam by a link structure which may have any one of the large number of different forms illustrated in the different embodiments discussed above.

In each of the embodiments, the beam is mounted in association with the housing by an isolator means which, in certain embodiments, comprises a separate element, and in other embodiments, comprises a portion of the frame secured directly or indirectly to the housing.

The invention comprehends that, in certain of the embodiments, the frame diaphragm and link be formed integrally as a one-piece molded element of a suitable synthetic resin, such as polycarbonate resin. Alternatively, as discussed above, the invention comprehends forming the elements of the force collector separately and effecting a bonded connection therebetween either by fusion bonding or by adhesion bonds, such as by an epoxy resin adhesive.

Each of the different forms of pressure transducer lends itself to economical manufacture by mass production. Further, the electrical connections to the strain gage bridge may be readily effected by means of the flat conductor cable 27 being brought into the pressure transducer chamber 15 through the housing in the conduit 59, with the connection between the cable and the strain gage bridge being effected by the fine wires 57, as illustrated in FIG. 3.

The invention comprehends that the elasticity in the strain gage be provided primarily by the beam rather than by the diaphragm or piston. In the illustrated embodiment, the beam comprises a single crystal deflecting member, such as a silicon wafer member. The strain gage bridge may be diffused into the silicon wafer surface and calibration of the system may be readily effected as discussed above by trimming of the external resistors 62 for further effectively minimizing cost of manufacture.

By utilizing different materials in the link, as shown in a number of the embodiments, automatic temperature compensation may be provided, further effectively minimizing the cost of the system.

By utilizing the improved flow control valve 14, a pressure relief to the pressure chamber 13 is provided, thereby further permitting effective minimization of cost of the pressure transducer by eliminating the need for high pressure protective means. More specifically, whenever a high pressure condition exists in the pressure chamber, the pressure will be relieved outwardly through the valve which may move from engagement with O-ring 47 against the resilience of the tubular resilient member 49 so that high pressure surges will be relieved to the sterile solution supply bag, avoiding damage to the pressure transducer.

The use of a synthetic resin, such as polycarbonate plastic, for a major portion of the components of the system provides a low cost, mass producible structure.

As discussed, as a result of the several above discussed features providing low cost of manufacture of the system, the cost thereof is effectively maintained at a sufficiently low level as to effectively permit the device to be considered as a throwaway, one-time use physiological pressure sensing system. Thus, the invention solves a serious problem in clinical pressure sensing operations of possible cross-contamination and infection by completely eliminating the need for the reuse of any of the system components by transfer from one patient to another. As discussed above, the elimination of the need for cleaning and resterilization of any of the components effectively improves the reliability of the system, solving another vexatious problem in such clinical pressure sensing operations.

In use, the pressure sensing system 10 is set up, as illustrated in FIG. 1, with the device 11 interconnected between the source of sterile solution, the output monitoring device, and the patient. As shown in FIG. 1, the connector 21 provides a ready connection to the source of sterile solution 18. The connector 28 provides means for readily connecting the device to the monitor connector 29, and the connector 22 provides means for readily connecting the device to the catheter 33 through the connector 31.

The stopcock connector 22 permits the taking of blood samples by the suitable selective positioning of the handle 25 so as to discharge blood from the patient through the connector 24. The stopcock is arranged so as to close all connections, when desired.

As discussed above, the fast flush valve is readily manually operable by the simple depression of the finger actuated portion 38 of operator 35. Thus, the initial filling of the system with sterile solution may be effected by opening of the valve 14 by the depression of handle portion 38. As discussed above, in the closed position of the valve, a small flow passage is maintained through the ports 43 and capillary bore 42 so as to continuously provide a flow of sterile saline solution through the system and catheter so as to maintain the catheter unclogged as by the patient's blood constituents.

The device may be maintained connected to the patient notwithstanding the application of high potentials to the patient, such as defibrillation potentials as the pressure transducer sensing strain gage is electrically isolated from the fluid in the pressure chamber. As indicated above, the electrical isolation further prevents injury to the patient as from electrical potentials appearing on the sensor beam as from electrical failure of the output elements, such as monitor 26.

As the cost of the device 11 is relatively low, upon completion of the use thereof with a given patient, the entire device, up to and including the connectors 21, 28 and 22, as well as the patient line, may be discarded so as to effectively eliminate any possibility of cross-contamination with other patients. Such low cost is effected in device 11 while yet providing high accuracy which is necessary for accurate clinical determinations.

The foregoing disclosure of specific embodiments is illustrative of the broad inventive concepts comprehended by the invention.

We claim:

1. A physiological pressure monitoring apparatus having a housing defining a fluid chamber and a wall portion provided with an aperture opening to said fluid chamber, and pressure transducer means mounted in said housing and responsive to fluid pressure in said fluid chamber for providing a corresponding electrical output signal, said pressure transducer means comprising:
a force collector comprising a compliant diaphragm, means sealingly bonding said diaphragm to said housing well portion about said aperture so that said diaphragm will be deflected by fluid pressure variations in the chamber, a frame defining a through opening aligned with said aperture and having a portion connected to said diaphragm about said opening, and a link connected to the diaphragm and extending longitudinally through said opening;
a resiliently deflectible beam;
strain gage means carried by the beam for providing an electrical signal corresponding to the amount of deflection of the beam;
isolator means mounting a first portion of the beam to the frame with a second portion of the beam juxtaposed to said link;
means securing said second portion of the beam to said link for movement with said link as an incident of deflection of said diaphragm and causing said strain gage means to produce an electrical signal corresponding to the amount of deflection of said beam produced by said movement; and
electrical conductor means connected to said strain gage means for electrically connecting said strain gage means to monitoring apparatus externally of said housing.

2. The physiological pressure monitoring apparatus of claim 1 wherein said link and diaphragm comprises a one-piece element having said diaphragm, frame, and link integrally joined.

3. The physiological pressure monitoring apparatus of claim 1 wherein said link and diaphragm comprise a unitary element.

4. The physiological pressure monitoring pressure of claim 1 wherein said link and diaphragm are formed of similar materials.

5. The physiological pressure monitoring apparatus of claim 1 wherein said link and diaphragm are formed of similar resinous materials and are joined by a solvent bond.

6. The physiological pressure monitoring apparatus of claim 1 wherein said diaphragm and housing are formed of similar materials.

7. The physiological pressure monitoring apparatus of claim 1 wherein said diaphragm and housing are formed of similar materials and are sealingly bonded by a solvent bond.

8. The physiological pressure monitoring apparatus of claim 1 wherein said means for securing said second portion of the beam to said link comprises an adhesive bond.

9. The physiological pressure monitoring apparatus of claim 1 wherein said beam is formed of silicon.

10. The physiological pressure monitoring apparatus of claim 1 wherein said beam comprises a wafer having a thickness of approximately 0.01 inches.

11. The physiological pressure monitoring apparatus of claim 1 wherein said electrical conductor means include a cable of conductors and fine wires connecting the strain gage means to said conductors.

12. The physiological pressure monitoring apparatus of claim 11 wherein the ends of said conductors are secured to said isolator means.

13. The physiological pressure monitoring apparatus of claim 11 wherein the ends of said conductors are secured to said isolator means in spaced relationship to said beam.

14. The physiological pressure monitoring apparatus of claim 1 wherein said frame comprises an annular element having a coaxial annular rib joined to said diaphragm.

15. The physiological pressure monitoring apparatus of claim 1 wherein said diaphragm is solvent-bonded to said housing.

16. The physiological pressure monitoring apparatus of claim 1 wherein said link comprises a stepped cylindrical element.

* * * * *